US009355474B2

(12) United States Patent
Celi et al.

(10) Patent No.: US 9,355,474 B2
(45) Date of Patent: May 31, 2016

(54) METHOD OF PROCESSING OPTICAL COHERENCE TOMOGRAPHY IMAGES

(71) Applicants: Consiglio Nazionale delle Ricerche, Rome (IT); Fondazione Toscana Gabriele Monasterio per la Ricerca Medica e di Sanità Pubblica, Pisa (IT)

(72) Inventors: Simona Celi, Rome (IT); Sergio Berti, Pisa (IT)

(73) Assignees: Consiglio Nazionale delle Ricerche, Rome (IT); Fondazione Toscana Gabriele Monasterio per IA Ricerca Medica e di Sanita Pubblica, Pisa (IT)

( * ) Notice: Subject to any disclaimer, the term of this patent is extended or adjusted under 35 U.S.C. 154(b) by 0 days.

(21) Appl. No.: 14/411,268

(22) PCT Filed: Jun. 28, 2013

(86) PCT No.: PCT/IB2013/055320
§ 371 (c)(1),
(2) Date: Dec. 24, 2014

(87) PCT Pub. No.: WO2014/002067
PCT Pub. Date: Jan. 3, 2014

(65) Prior Publication Data
US 2015/0213629 A1    Jul. 30, 2015

(30) Foreign Application Priority Data

Jun. 29, 2012 (IT) .............................. MI2012A1156

(51) Int. Cl.
*G06K 9/00* (2006.01)
*G06T 11/00* (2006.01)
(Continued)

(52) U.S. Cl.
CPC ............. *G06T 11/005* (2013.01); *A61B 5/0066* (2013.01); *A61B 5/02007* (2013.01);
(Continued)

(58) Field of Classification Search
CPC ............... A61B 5/0066; A61B 5/0084; A61B 5/02007; G06T 7/0012; G06T 7/0079; G06T 7/60; G06T 2207/10101; G06T 2207/20116; G06T 7/0002; G06T 11/005; G06T 2207/30101

USPC ........................................................ 382/128
See application file for complete search history.

(56) References Cited

U.S. PATENT DOCUMENTS

2008/0051658 A1    2/2008 Demi et al.
2008/0075375 A1    3/2008 Unal et al.
(Continued)

OTHER PUBLICATIONS

Sihan et al., "Fully Automatic Three-Dimensional Quantitative Analysis of Intracoronary Optical Coherence Tomography: Method and Validation", Catheterization and Cardiovascular Interventions, 2009, pp. 1058-1065, vol. 74.
(Continued)

*Primary Examiner* — Gregory F Cunningham
(74) *Attorney, Agent, or Firm* — Alan G. Towner, Esq.; Pietragallo Gordon Alfano Bosick & Raspanti, LLP

(57) ABSTRACT

An automatic or semiautomatic method of processing intravascular Optical Coherence Tomography (OCT) images, comprising: pre-processing the primary image by segmenting the guidewire in the lumen to exclude it from the image, determining whether the lumen is open or closed; if the lumen is determined to be closed, performing a first automatic lumen segmentation procedure on the pre-processed image to define a perimeter line of the lumen, corresponding to the inner edge of the vessel wall, and determine a centroid CL of the lumen area; if the lumen is determined not to be closed, sequentially performing an automatic lumen closing procedure on the pre-processed image, and a second automatic lumen segmentation procedure, to define a perimeter line of the lumen, corresponding to the inner edge of the vessel wall, and determine a centroid CL of the lumen area; automatically finding an outer edge of the vessel wall and defining a first region of interest $ROI_1$ between the inner edge and the outer edge of the lumen; automatically segmenting a fibrous plaque in the first region of interest $ROI_1$ thereby defining a second region of interest $ROI_2$ that contains the fibrous plaque, and segmenting a hyporeflective plaque, contained in a radial region that falls within $ROI_1$ and is external to $ROI_2$.

15 Claims, 11 Drawing Sheets

(51) Int. Cl.
- *A61B 5/00* (2006.01)
- *G06T 7/00* (2006.01)
- *G06T 7/60* (2006.01)
- *A61B 5/02* (2006.01)

(52) U.S. Cl.
CPC ............ *G06T 7/0002* (2013.01); *G06T 7/0012* (2013.01); *G06T 7/0079* (2013.01); *G06T 7/60* (2013.01); *A61B 5/0084* (2013.01); *G06T 2207/10101* (2013.01); *G06T 2207/20116* (2013.01); *G06T 2207/30101* (2013.01)

(56) References Cited

U.S. PATENT DOCUMENTS

| | | |
|---|---|---|
| 2011/0071404 A1 | 3/2011 | Schmitt et al. |
| 2012/0075638 A1* | 3/2012 | Rollins et al. .................. 356/479 |

OTHER PUBLICATIONS

Tsantis et al., "Automatic vessel lumen segmentation and stent strut detection in intravascular optical coherence tomography", Med. Phys., Jan. 2012, pp. 503-513, vol. 39 (1).

* cited by examiner

METHOD OF PROCESSING OPTICAL COHERENCE TOMOGRAPHY IMAGES

FIELD OF INVENTION

The present invention concerns the field of medical image processing and particularly relates to a method of processing Optical Coherence Tomography images.

STATE OF THE ART

The cardiovascular disease is still one of the diseases with the highest social relevance, and is one of the major causes of death in developed countries. In this context, atherosclerosis is, according to a many statistical studies, the main cause of very serious cardiovascular diseases, such as angina pectoris, infarction, ictus and sudden death. As a result, the ability to assess the structure of arterial walls, as well as their morphology is important in defining diseases (and their progression) and planning pharmacological therapies and surgery.

Optical Coherence Tomography (OCT) is a relatively recent imaging technique, which provides cross sectional optical images of blood vessels having lumens to about 4 mm, with axial and lateral resolutions of about 10 μm and 20 μm, respectively.

The resolution level attained in the art allows visualization of inner coronary structures, intimal thickening, thickness of the fibrous plaque and distinction of the main tissue constituents.

An extensive review of the image acquisition methodology and clinical applications of OCT is contained in "*Expert review document on methodology, terminology, and clinical applications of optical coherence tomography: physical principles, methodology of image acquisition, and clinical application for assessment of coronary arteries and atherosclerosis*" by F. Prati et al., published in European Heart Journal, vol. 31 (2010), pages 401-415.

Quantitative assessment of vascular disease from a cross sectional OCT image usually requires various quantitative measurements, such as the cross sectional area of the vessel, the average diameter and the resistance to blood flow, which shall be often based on accurate identification of the edge of blood vessel lumen.

Patent Application US 2011/0071404 discloses a method of automatic assessment of a region of a lumen, which comprises the steps of: collecting a set of data regarding a vessel segment of length L using an optical coherence tomography system, the set comprising a plurality of cross sectional areas at a plurality of positions along the length; determining a vascular resistance ratio using a processor and at least a portion of the set of data; and determining a characteristic of at least a portion of the region disposed along the length L in relation to the vascular resistance ratio. The vascular resistance ratio is a measurement of the severity of the stenotic lesion reproduced in the OCT image. In US 2011/001404, the missing vessel profile data in the image are interpolated using interpolation functions.

Patent application US 2012/0075638 discloses a method of automatic or semi-automatic segmentation and quantification of blood vessel structure and physiology, using an OCT system. The method comprises: obtaining an OCT image set comprising one or more images of a portion of a blood vessel; segmenting a portion of at least one instrumental image which emits and receives an OCT signal; segmenting a vessel wall portion and segmenting a calcified plaque portion.

Upon diagnosis of a serious stenosis of a blood vessel in a patient, the patient may undergo percutaneous transluminal angioplasty procedures, which involve application of one or more stents injected into the longitudinal region of the vessel, at the constriction, to restore the normal vessel diameter.

The application WO 2011/135103 is directed to a computer-implemented method for analyzing the behavior of a transluminal implant, e.g. a coronary implant device. The method comprises analyzing multiple images from in-vivo acquired OCT images, recorded with a freshly implanted device and at subsequent times, of long vessel segments of the transluminal implant device formed by strut from bars or of a longitudinal tubular implant device formed by strut from bars in a vessel, the method comprising automatic contouring and identifying structures of the in-vivo acquired images, segmenting the implant device and lumen based on A-scan analysis by (1) a bright reflection, (2) a shadow and (3) a rapid rise and fall of energy, scan conversion of the image to a fast analysis platform, evaluation of strut apposition or strut coverage from A-line segmentation in the scan-converted image, wherein said method provides automatic identification and measurement of both the 1) distance of the separate surfaces zones of the implant device to the vessel wall (apposition) and the 2) neointima coverage, corresponding to vessel healing after implantation of the implant device.

SUMMARY OF THE INVENTION

The Applicant found that it would be advantageous to provide a method of processing intravascular OCT images, which allows the main coronary microstructures to be identified with sufficient accuracy, while reducing the processing time by various orders of magnitude as compared with a manual method of identifying the main microstructures.

One of the main characteristics of the present invention is segmentation of tissues according to a hierarchic image processing flow, to highlight the region of interest to be investigated.

As used herein, image segmentation is generally intended as a digital method to divide an image into regions that may consist of a pixel area that is homogeneous in terms of certain characteristics, or of an area that groups all the pixels corresponding to an object that is visualized in the image. In this way, multiple layers or image fragments may be created, for example with the aim of separating objects from the rest of the image.

In one aspect, the present invention relates to an automatic or semiautomatic method of processing intravascular Optical Coherence Tomography (OCT) images, comprising:
- receiving in a computer a primary cross-sectional OCT image, visualizing a section of a blood vessel having a lumen and a vessel wall;
- pre-processing the primary image by the computer, wherein the pre-processing step comprises segmenting a guidewire in the lumen and excluding the guidewire from the primary image, to obtain a pre-processed image;
- determining whether the lumen is closed;
- if the lumen is determined to be closed, performing a first automatic lumen segmentation procedure on the pre-processed image to define a perimeter line of the lumen, corresponding to the inner edge of the vessel wall, and determine a centroid $C_L$ of the lumen area;
- if the lumen is determined not to be closed, sequentially performing an automatic lumen closing procedure on the pre-processed image, and a second automatic lumen segmentation procedure, to define a perimeter line of the lumen, corresponding to the inner edge of the vessel wall, and determine a centroid $C_L$ of the lumen area;

automatically finding an outer edge of the vessel wall and defining a first region of interest $ROI_1$ between the inner edge and the outer edge of the vessel wall;

automatically segmenting a fibrous plaque within the first region of interest $ROI_1$, thereby defining a second region of interest $ROI_2$ that contains the fibrous plaque, and segmenting a hyporeflective plaque, contained in a radial region that falls within $ROI_1$ and is external to $ROI_2$.

In certain embodiments, in the step of pre-processing the primary image, the step of segmenting the guidewire comprises:

creating a sub-image in a central portion of the primary image;

transforming said sub-image into a binary image using a digital binarization filter that defines a light intensity threshold value or a range of light intensity threshold values to generate a sample image, highlighting one or more regions having a high light intensity relative to a background;

applying a morphological filter to the sample image, which filter sequentially uses a morphological operator of recognition and extraction of objects having a round shape and a morphological erosion operator to eliminate small non-round objects so as to identify a round object associated with the guidewire; and calculating the area of the identified round object and calculating a local centroid $C_w$ of said area.

Preferably, in the step of pre-processing the primary image, the step of excluding the guidewire from the primary image comprises:

restoring the primary image, and subtracting the round object associated with the previously segmented guidewire from the primary image, to generate a subtraction image corresponding to the pre-processed image.

Preferably, the step of creating a sub-image in a central portion of the primary image is carried out in accordance with one of the following steps:

applying a digital crop filter by a process of selection and extraction of a primary image central portion from the primary image, and selecting by an operator an image portion in the lumen.

In certain embodiments, the first automatic lumen segmentation procedure comprises:

transforming the pre-processed image into a binary image using a digital binarization filter, to define an annular vessel wall region, relative to a background, defining a lumen area as an area of an image portion enclosed and delimited by the annular vessel wall region;

defining a perimeter line of the lumen, which corresponds to the contour of the lumen area, and determining a centroid $C_L$ of the lumen area.

In certain embodiments, the step of segmenting the guidewire comprises defining a centroid $C_w$ of the guidewire area, and wherein the automatic lumen closing procedure and the second automatic lumen segmentation procedure comprise:

transforming the image resulting from the pre-processing step into a binary image, by applying a digital binarization filter that generates a region BW1 associated with the vessel wall highlighted against a background, the region BW1 exhibiting a radial discontinuity in light intensity, in at least one radial portion of the lumen;

contouring the BW1 region on the binary image;

drawing a plurality of radial lines originating from the centroid $C_w$ of the guidewire and radially extending through the region BW1;

determining an intersection point $IP_L$ between each radial line and the wall as a point having the minimum distance from the centroid $C_w$ of the guidewire area along the same radial line to obtain a plurality of intersection points $IP_L$;

generating a perimeter line for closing the lumen by interpolation of the intersection points $IP_L$, and calculating the lumen area as an area enclosed and delimited by the perimeter closing line and determining a centroid $C_L$ of the lumen area.

Preferably, the method further comprises, after transforming the pre-processed image into a binary image and before contouring the region BW1, the step of applying an opening-closing morphological filter to the region BW1.

Preferably, the step of automatically finding an outer edge of the vessel wall and defining a first region of interest $ROI_1$ comprises:

selecting a preset wall thickness value;

drawing a plurality of radial lines originating from the centroid $C_L$ of the lumen and extending through the vessel wall, the plurality of radial lines having a radial distribution extending along a circumference;

determining the intersection point between each radial line and the perimeter line of the lumen, the perimeter line as determined in the first or in the second automatic segmentation procedure;

determining an external point $IP_E$ by adding, along each radial line, the preset thickness value from the intersection point between such radial line and the perimeter line of the lumen;

defining an outer edge as the perimeter line obtained by joining the points $IP_E$ identified for each radial line, and defining a first region of interest $ROI_1$ as an image portion delimited by the perimeter line of the lumen and the outer edge.

Preferably, the step of automatically segmenting the fibrous plaque comprises:

applying a digital decorrelation stretching filter in the first region of interest $ROI_1$;

selecting a homogeneous image region having an intensity higher than a preset threshold value by applying a binarization filter to the image resulting from the application of the digital decorrelation stretching filter;

applying a opening-closing morphological filter to the homogeneous region;

contouring the homogeneous region, and identifying the resulting homogeneous region as the second region of interest $ROI_2$.

Preferably, after the step of segmenting the fibrous plaque, the method further comprises a step of automatically quantifying the angular extent of the fibrous plaque region, which comprises:

drawing a plurality of radial lines originating from the centroid $C_L$ of the lumen and extending through the $ROI_1$, the plurality of radial lines having an angular distribution with an angular pitch defined between two proximal radial lines;

determining, for each radial line of the plurality, whether such radial line intercepts one point of the fibrous plaque region;

selecting a sub-plurality of radial lines, which intercept the second region of interest $ROI_2$ and determining the angular extent of $ROI_2$ according to the number of the sub-plurality of radial lines and the angular pitch between two proximal radial lines of the sub-plurality.

In certain embodiments, the step of segmenting the hyporeflective plaque comprises:

receiving, by an operator, geometric data defining a preliminary hyporeflective region that contains vessel wall tissues and is external to the second region of interest $ROI_2$, wherein the preliminary region has a contour;

automatically checking whether the preliminary region falls within the first region of interest $ROI_1$;

in the negative, repeating the step of receiving geometric data;

in the positive, carrying out the steps of:

storing the contour of the preliminary region;

calculating a maximum light intensity value, a minimum light intensity value and a mean intensity value between the maximum and minimum values, within the preliminary region;

transforming the image into a binary image by means of a band-pass threshold filter that selects the intensity values ranging between the maximum and the mean light intensity values to identify image portions having a prevailing fibrous component within the preliminary region, and applying a convex hull morphological filter, to define a hyporeflective plaque region having a continuous contour.

Preferably, the step of segmenting the hyporeflective plaque comprises, before the step of receiving geometric data defining a preliminary hyporeflective region, a step of automatically obscuring at least partially the second region of interest $ROI_2$.

Preferably, after the step of segmenting the hyporeflective plaque, a step of automatically quantifying the hyporeflective plaque, which comprises:

drawing a plurality of radial lines which pass through the centroid $C_L$ of the lumen and radially extend at least through the hyporeflective plaque region, the plurality of radial lines having an angular distribution with an angular pitch defined between two proximal radial lines;

determining, for each radial line of the plurality, whether such line intercepts one point of the hyporeflective plaque region;

selecting a sub-plurality of radial lines, which intercept the hyporeflective plaque region, and determining the angular extent of hyporeflective plaque region according to the number of the sub-plurality of radial lines and the angular pitch between two proximal radial lines of the sub-plurality.

The method may find application in off-line assessment of intravascular coronary anomalies.

The method may also find application in off-line assessment of stresses on the vessel wall induced by a rotational atherectomy, which often precedes stent apposition.

BRIEF DESCRIPTION OF THE DRAWINGS

Further features and advantages of the invention will become readily apparent from the following description, referring to non-limiting exemplary embodiments of the invention and to the annexed figures, in which:

FIG. 4d shows the result of the application of the binarization filter to the sub-image selected in FIG. 4a.

DETAILED DESCRIPTION

Figure 1:
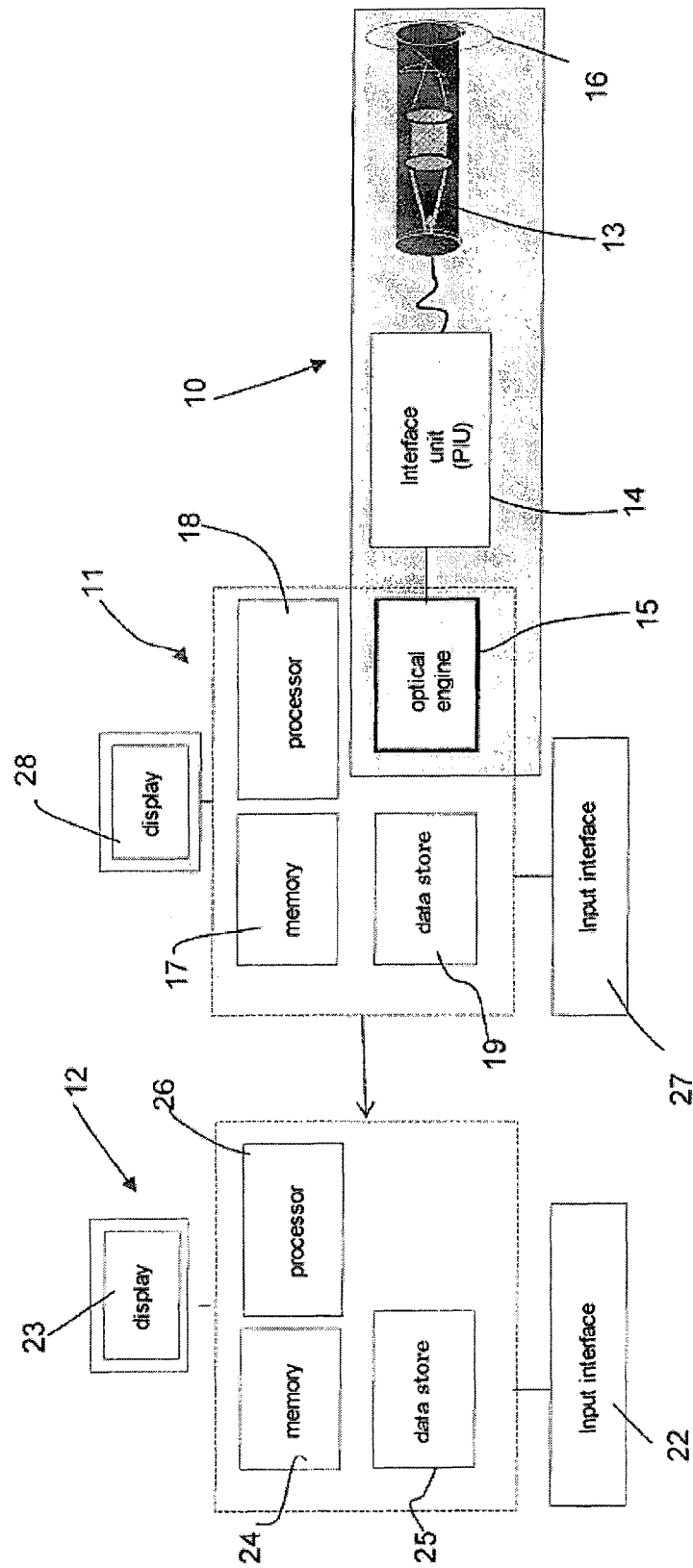
FIG. 1 is a schematic diagram of an exemplary OCT image acquisition and processing system, suitable for generating images that can be processed with the method of the present invention.

A cross-sectional OCT image is acquired by an OCT imaging system, known per se. FIG. 1 shows a schematic diagram of an exemplary OCT image acquisition and processing system, which is adapted to generate intravascular images that can be processed with the method of the present invention. The system comprises an OCT measurement system 10, an acquisition unit 11 and a data processing unit 12. The acquisition unit 11 comprises a memory 17, possibly connected to a database 19, a processor 18 and an optical imaging engine 15. The acquisition unit further comprises an input interface 27 and a display device 28 for displaying the acquired images.

The imaging engine comprises a light source, generally an infrared LED, a polarization-diversity interferometer and a system for detecting the signal backscattered from the analyzed sample and a reference signal (elements inside 15 not shown). The imaging engine is optically connected via an optical fiber to a Probe Interface Unit (PIU) 14, which is in turn optically connected to a catheter 13 having a transparent sheath, via an optical fiber. The catheter includes an optical fiber (not shown) with a rotating microlens 16 placed at one end thereof. For longitudinal scanning of a blood vessel, the PIU 14 contains a motorized mechanism that retracts the optical fiber into the transparent sheath of the catheter as the fiber rotates. The imaging engine, the PIU and the catheter are the main elements of the OCT measurement system 10.

As used in the present disclosure and claims, a guide wire shall be intended as the probe assembly connected to and downstream from the interface unit (PIU), and typically comprising the catheter and the optical fiber that optically connects the catheter to the PIU.

The OCT technique operates by low coherence interferometry, which utilizes the reflection of a light wave beam in the infrared region, i.e. from 1000 to 1300 nm. For vessel wall analysis, a catheter is introduced into the lumen to the segment to be analyzed. The light beam is focused and directed to the vessel wall through the optical fiber. The catheter acts as a probe and emits a light beam which is partially absorbed by the tissue and partially reflected. In time-domain OCT, the structures in the vessel are visualized by processing the reflection time generated by the various structures. This operation is carried out by the polarization-diversity interferometer included in the imaging engine, which compares the light that is reflected by the sample being analyzed with a reference beam.

The system detects the reflected light by sampling points along a radius originated from the center of the catheter at the greatest image depth to the light of the center of the catheter, which is called "A-scan" line. A sequence of scan lines is collected as the catheter rotates, and a full rotation of the catheter generates a cross-sectional OCT image. Longitudinal scanning is allowed by a pull-back system located in the PIU, which is adapted to pull back the microlens. The pull-back speed of the catheter is, for example, about 3 mm/s, which affords the acquisition of about 15/20 images per second.

Commercial OCT systems generally provide, as an output, a digital image consisting of a pixel matrix in which the size of an individual pixel approximately represents the spatial resolution of the image. The acquired images are usually displayed in gray-scale or red-green-blue false color scale (RGB). The conversion of the size of an individual pixel into physical quantity units is typically based on the knowledge of the real dimensions of an object that is designed to be visualized by an OCT image, e.g. of the catheter.

Referring to the system of FIG. 1, at the end of an OCT measurement or after measurement of a set of OCT cross sections, the acquisition unit 11 transmits one or more cross-sectional OCT images to an image processing unit 12. The processing unit comprises a processor 26, a memory 24 and a data store 25. In the usual way, the processing unit 12 has an input interface 22, connected to input devices such as a mouse, a keyboard or a touch-screen display, and an image display device 23, such as a computer screen.

In an OCT image, detection of coronary microstructures depends on the behavior of the latter in response to the light that impinges thereon. Generally, highly reflective microstructures, such as the plaque having a mainly fibrous composition, are more visible to the naked eye of an operator that would manually analyze images. The Applicant found that the presence of highly reflective microstructures may prevent naked-eye detection of other poorly reflective microstructures, that will not be highlighted.

FIGS. 2a-2d show examples of cross-sectional OCT images, identifying tissues in a cross section of an undiseased blood vessel and in cross sections of blood vessels characterized by various anomalies.

The images of FIGS. 2a-2d relate to OCT cross sections as acquired by a commercial time-domain OCT system M2/M3, manufactured by LightLab. Images were acquired at a wavelength of 1.3 μm with 10-20 μm axial resolution and 25-40 μm lateral resolution. The images that are shown in the subsequent figures are or have been processed from primary images, using the same OCT system as in images of FIGS. 2a-2d. Nevertheless, the method of the present invention shall be intended to apply to OCT cross-sectional images obtained using any type of OCT, such as those in the optical frequency-domain and with the technique known as "Fourier Domain".

Figure 2B:
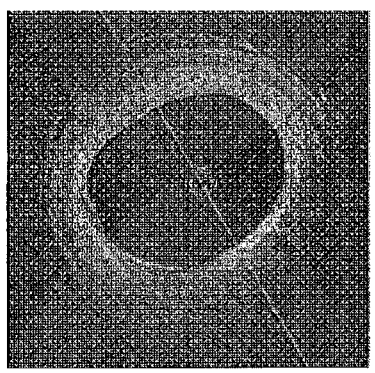
FIGS. 2a-2d show examples of cross-sectional OCT images, identifying tissues in a cross section of an undiseased blood vessel and in cross sections of blood vessels characterized by various anomalies.
Figure 2D:
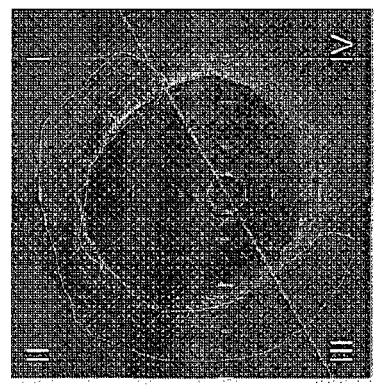
Figure 2A:
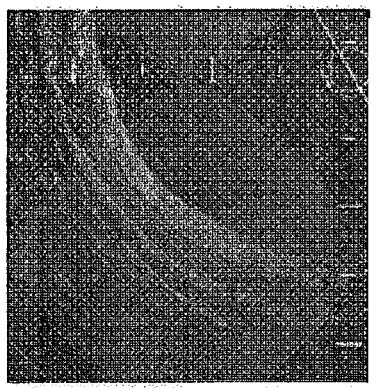

FIG. 2a is a portion of a vessel image that shows no disease or a vessel analyzed in a longitudinal position, where atherosclerotic plaques are absent or are very thin. The vessel wall is shown to consist of three concentric coats: an inner elastic coat, known as tunica intima, which delimits the lumen; a middle coat, known as tunica media, consisting of muscle fibrocells and elastic fibers, and an outer elastic coat, known as tunica adventitia. In the image, the tunica media is detected as a "dark" hyporeflective area, delimited by the tunica intima, which is defined by a relatively high brightness and by the tunica adventitia, defined by a bright, heterogeneous signal. Generally, the wall thickness of a "normal" vessel does not exceed 1.2 mm and the three layers that form the vessel wall may be distinguished in the image. In FIG. 2a, the guide wire is shown as a small circle on the bottom right, and relative to the lumen, in an approximately central position. Only a portion of the image of the lumen is shown in FIG. 2a, to highlight the three-layer structure of the wall.

In case of atherosclerosis, the tunica media is typically thinned in the wall quadrants that contain accumulated plaque (or atheroma), resulting in asymmetric wall expansion. Fibrous tissues, or fibrous plaques, are generally visualized as a bright region close to the lumen, whereas plaques with a mainly fibrocalcific plaque appear as a region having a low signal reflectivity, and hence a dark appearance, but with well-defined edges, and mainly lipid plaques appear as regions having a poor signal reflectivity with blurred edges.

Figure 2C:
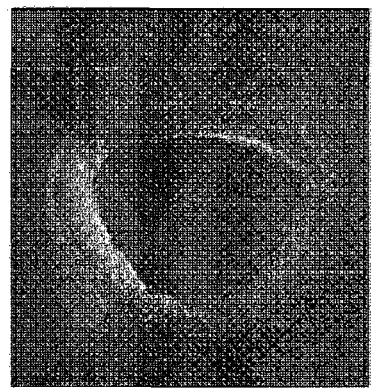

FIG. 2b shows a section of a vessel with the tunica intima thickened over the entire wall. In FIG. 2c a thin fibrous hood appears on the inner wall, which narrows the vessel lumen and is visible as a brighter region located on the top left of the image.

In the image of FIG. 2d, which is divided into quadrants I to IV, a fibrocalcific plaque is found, which extends radial to the lumen over about 260° and is present in the quadrants I, II and III. A white contour was manually added to the image, to approximately indicate the extension of the fibrocalcific plate.

In an OCT image as acquired by the system, the guide wire may create a very bright artifact, which is generally much brighter than the other structures of the image, whose brightness depends on which portion of the guide wire is visualized. For example, the image shows a very bright region at the end of the wire (i.e. the light beam emitting point) and a shadow cone originating from the bright end.

Without limiting the present invention to a particular relationship between the nature of pathological anomalies and the OCT image that represents them, Table 1 shows how certain coronary microstructures are shown in OCT images in most cases.

TABLE 1

| Histology | OCT visualization |
|---|---|
| Intima | High-reflectivity layer close to the lumen |
| Tunica media | Hyporeflective layer in the middle of the vessel wall |
| Adventitia | Outer layer of the high-reflectivity wall |
| Fibrous plaque | Homogeneous high-reflectivity area |
| Calcific plaque | Heterogeneous hyporeflective area with well-defined, but generally irregular edges |
| Lipid plaque | Homogeneous hyporeflective area with blurred edges, and high signal attenuation by the tissues |
| Fibrous hood | High reflectivity layer overlapping a hyporeflective area |

The penetration of the OCT signal in the radial direction originating from the guide wire is a function of the plaque composition. Maximum penetration is typically obtained in the case of fibrous tissue, with penetration progressively decreasing in mainly calcific tissues, in lipid plaque and in a thrombus.

Figure 3:
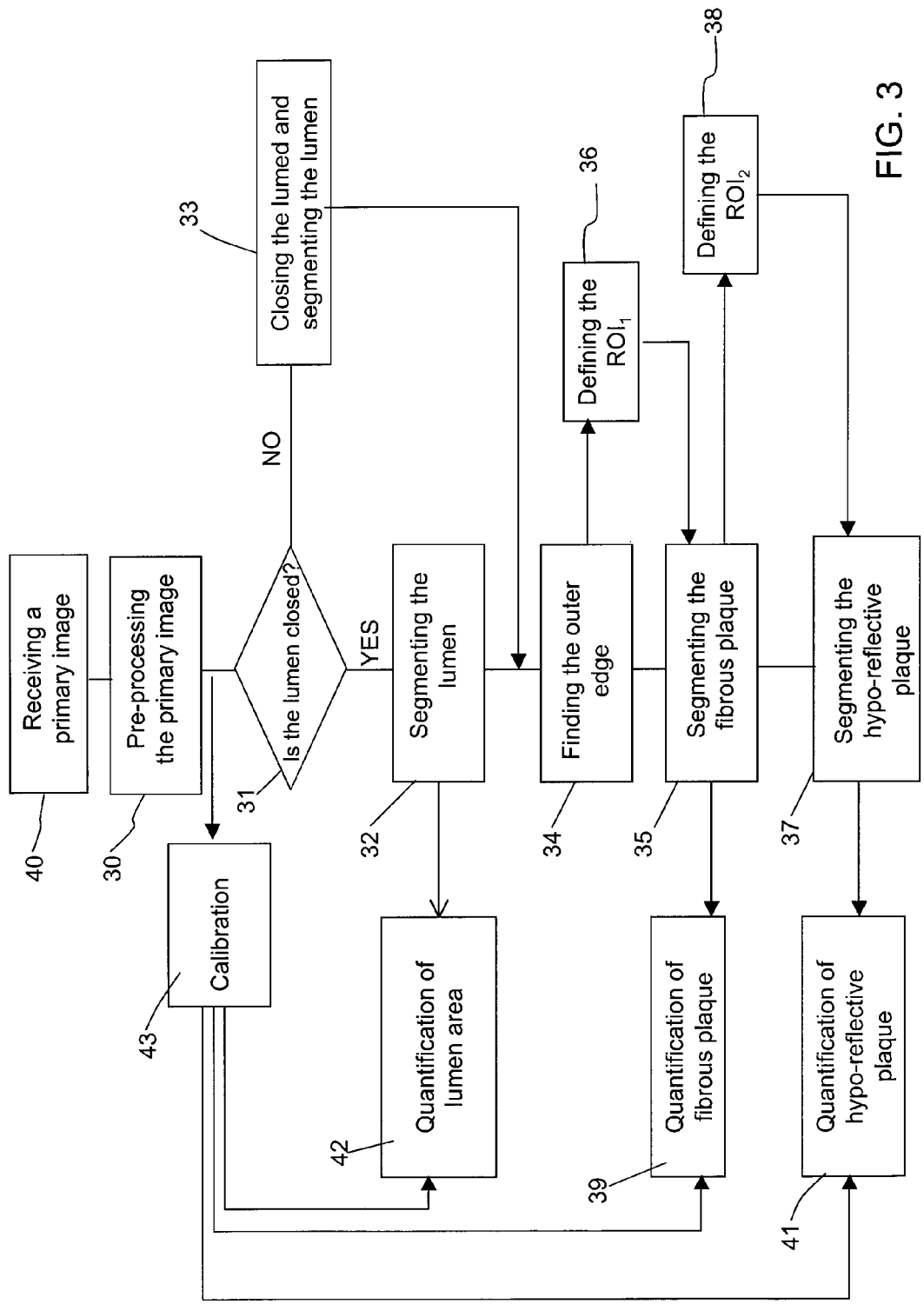
FIG. 3 is a flow diagram of a method of processing cross sectional OCT images according to an embodiment of the present invention.

FIG. 3 is a flow diagram of a method of processing cross sectional OCT images according to an embodiment of the present invention. The method comprises receiving a primary cross-sectional OCT image, which visualizes a cross section of a blood vessel (step 40). As used herein, the term primary image is intended as the state of the original image as acquired and transmitted from the OCT measurement acquisition unit to the image processing unit, which loads it in its memory. The primary image may be a color-space encoded image, e.g. a RGB image, or an image having a one-dimensional light intensity, e.g. grey-scale.

Following reception of a primary image, the method comprises a step 30 of pre-processing the primary image, which involves wireguide segmentation for detecting the position and size of the guidewire, i.e. the area occupied by the guidewire in the image, and for removing the guidewire contribution from the primary image.

In a cross-sectional OCT image, the guidewire is typically located in a central region of the image.

Particularly, the pre-processing step 30 comprises segmenting the guidewire and excluding the guidewire from the primary image. In an embodiment, guidewire segmentation comprises finding the guidewire in the image by creating a sub-image of the primary image, through selection of a central portion of the primary image, creating a sample image by application of a digital binarization filter to the sub-image, applying a circular mask to the sample image to identify a round object in an image portion within the lumen, such round object being associated with the guidewire, determining the area of the identified round object and calculating the centroid $C_w$ of the area of the round object, herein referred also to as centroid of the guidewire. In one embodiment, the centroid is calculated as a center of mass of the area of the round object.

The digital binarization filter that is used to generate the sample image transforms the sub-image into a binary, i.e. two-tone image, which assigns a 1 value to the pixels whose light intensity exceeds a threshold value and a 0 value to the pixels whose intensity is equal to or lower than said threshold value (or a 1 value is assigned to the pixels that fall within a range of intensity values from first to second threshold values, and a 0 value is assigned to the pixels whose intensity does not fall in that range). Since the guidewire is typically visualized in an OCT image as a very bright region, the threshold value or the range of threshold values are selected from relatively high intensity values in the image, which may be automatically selected by a light intensity scan algorithm for light intensity scanning in the primary image.

The application of a circular mask comprises: applying a morphological filter, which sequentially uses a morphological operator of recognition and extraction of objects having a round shape and a morphological erosion operator to eliminate small non-round objects from the image portion in the lumen.

The morphological operator of recognition and extraction of round objects may use morphological mathematical algorithms such as Hugh transform or Eigen Object operators. The operator may alternatively use an algorithm for calculating a metric unit defined as $$M = \frac{4\pi A}{P^2} \qquad (1)$$

where A is the area, P is the perimeter and the value of M is the closer to 1 the more the shape of the relevant object approaches the round shape.

The use of a circular mask is advantageous in that, in OCT measurement systems, the guidewire has a circular shape and is often located in an approximately central position in the lumen, during acquisition of a cross-sectional OCT image.

The digital filters and digital masks as disclosed herein are obtained using mathematical algorithms suitable for image processing, and implemented by means of commercial software, such as MATLAB® or custom.

A sub-image may be created manually, with an operator selecting, by means of a computer, a crop portion of an image in the lumen, or automatically, by applying a crop filter according to preset values, from the center of the position of a sub-image and its dimensions.

After segmentation of the guidewire, the step of excluding the guidewire from the image comprises: restoring the primary image, i.e. deselecting the sub-image (e.g. removing the crop filter); subtracting from the primary image the intensity values of at least the pixels that compose the round object corresponding to the previously segmented guidewire, to generate a subtraction image. For example, subtraction of the intensity values of the pixels from the primary image comprises setting the intensity values of such pixels to zero, or setting the intensity values of such pixels to a background value, where the background value is determined, for instance, by calculating an average intensity value in a portion of the OCT primary image that is free of objects.

Preferably, before application of the circular mask, the pre-processing step comprises applying a morphological filter to the sample image, which filter uses an open-close algorithm to remove small foreign objects from the image and fill false fractures in the objects that fall within a region in the lumen.

The segmentation of the guidewire, which determines the contour and hence the dimension of the guidewire, allows calibration of the OCT images, whose dimensional units may be converted from image units (pixels) into metric units. FIG. 3 shows that the calibration step 43 is carried out after the pre-processing step 30.

Figure 4B:
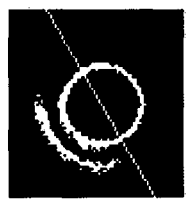
FIG. 4b shows the image of FIG. 4c, in which a portion of the image comprising the guidewire has been dimmed.
Figure 4A:
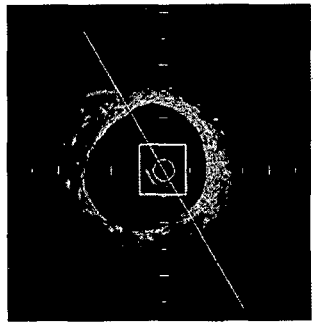
FIG. 4a shows a primary cross sectional OCT image in which a sub-image has been automatically selected in a portion of the lumen.

FIG. 4a shows a primary cross-sectional OCT image in which a sub-image has been automatically selected in the figure by means of a rectangle outlined with a solid white line. FIG. 4b shows the result of the application of the binarization filter to the sub-image selected in FIG. 4a. It shall be noted that, in the proximity of a circular high-intensity area, a further high-intensity area is provided, due to an artifact, which has an elongate shape and extends circumferentially above the circular area. The circular mask recognizes and extracts only the circular object.

Figure 4D:
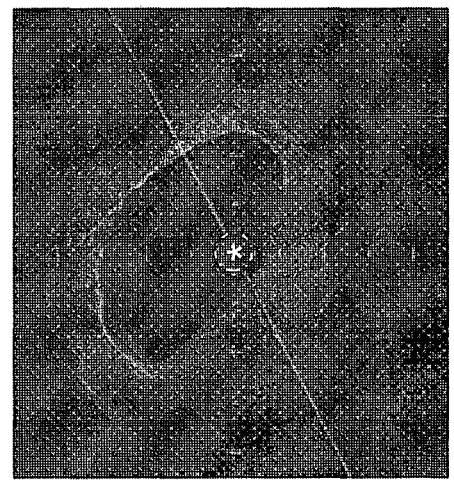
Figure 4C:
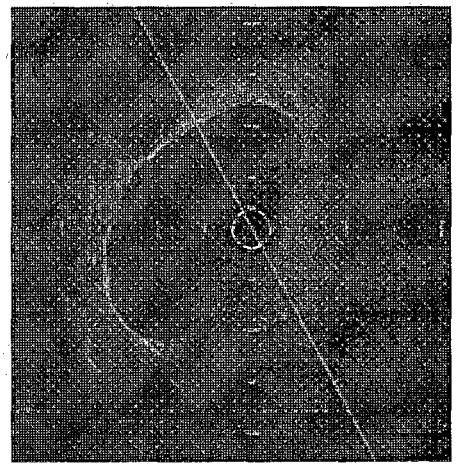
FIG. 4c shows an image resulting from a primary cross sectional OCT image, after a guidewire segmentation step.

FIG. 4c shows an image resulting from a primary OCT image (other than the image 4a) after segmentation of the guidewire, comprising application of a binarization filter and application of a circular mask to calculate $C_w$ and determine the contour of the guidewire. The image of FIG. 4c is the primary (restored) image in which the contour of the guidewire (dashed white line) is indicated. It shall be noted that, in the example of the figure, the guidewire is placed proximate to the vessel wall and hence the binarized sample image (not shown) also shows, in addition to the high-luminosity characteristics due to the guidewire, a vessel wall portion proximate to the guidewire. The application of a circular mask that finds round objects in the threshold image and highlights them allows isolation of the guidewire characteristics from those of the portion adjacent to the wall. In FIG. 4d a portion of the image of FIG. 4c comprising the guidewire has been dimmed. The white star symbol indicates the centroid $C_w$ of the guidewire and the dashed white line indicates the position of the guidewire which is no longer visible, as it is dimmed.

Optionally, in the pre-processing step 30 and after guidewire segmentation and subtraction of the guidewire from the primary OCT image, the resulting image is filtered to reduce any speckle (excessive roughness of the image) by applying a two-dimensional digital median filter which operates by rounding off the maximum and minimum image intensity values, particularly by eliminating the values below a minimum preset value. The median filter is known per se and is a particular type or rank algorithm, which operates on each pixel of the image by analyzing a pixel window directly surrounding the starting pixel, with the neighboring pixels being sorted in ascending order. The starting pixel is assigned a value that corresponds to the average of those of the neighboring pixels. Other filtering arrangements may be used to reduce image speckle, for example a Gaussian filter.

Preferably, the position of the guidewire in the pre-processed image is highlighted, although the guide wire is dimmed, for instance as is typical, by overlapping lines or dots having a well-defined color or gray tone, e.g. using a broken line, as shown in FIGS. 4c and 4d.

Referring back to FIG. 3, after the pre-processing step 30, the method comprises a step 31 for determining if the vessel lumen is closed, i.e. if the lumen is visualized as having a solid delimiting edge. In the positive, the method moves to the vessel lumen segmentation step 32.

If the lumen is determined to be closed, the lumen segmentation step comprises:
(1) transforming the image that results from the pre-processing step (i.e. in which the guidewire is dimmed) into a binary image, so as to highlight the vessel wall against the background (and thus against the lumen) and defining an annular vessel wall region,
(2) after transforming the image into a binary image, defining a lumen area as an area (e.g. sum of pixels) of an image portion enclosed and delimited by the annular vessel wall region;
(3) defining a perimeter line of the lumen, which corresponds to the contour of the lumen area, and
(4) determining a centroid $C_L$ of the lumen area.

In one embodiment, the centroid of the lumen area is calculated as a center of mass of the area of the lumen.

The step of determining whether the lumen-delimiting edge is continuous is carried out manually, with an operator visualizing the pre-processed OCT image and, if the lumen is determined to be closed, instructing the processing unit, e.g. as is usual through the input interface, to proceed with the lumen segmentation step 32.

In a different embodiment, the step of determining whether the lumen-delimiting edge is continuous is automatically carried out by the system, for example by using an algorithm for automatically finding a radial light intensity discontinuity region in an image portion comprising the vessel wall and having a light intensity above a given threshold value.

In one embodiment, the step of determining whether the lumen-delimiting edge is solid (i.e. whether the lumen is closed) is an automatic determination step, which comprises:
 transforming the image that results from the pre-processing step into a binary image using a digital binarization filter, which will generate a region associated with the vessel wall, highlighted against a background;
 drawing a plurality of radial lines originating from (or passing through) the centroid $C_w$ of the guidewire and radially extending through the vessel wall;
 determining, for each radial line, whether at least one point of intersection with the region associated with the vessel wall exists;
 if no point of intersection is determined to exist for at least one radial line of the plurality of radial lines, the lumen is determined to be open;
 if at least one point of intersection is determined to exist for each radial line of the plurality of radial lines, the lumen is determined to be closed.

In one embodiment, if the lumen is determined to be closed, then the method proceeds to a first automatic segmentation procedure (step 32 of FIG. 3).

According to one embodiment, if the lumen is determined to be open, an automatic lumen closing procedure and a second automatic lumen segmentation procedure, as shown in FIG. 3 as step 33, are carried out. In this embodiment and referring to FIG. 6, which is described in greater detail below, from the at least one point of intersection with the region associated with the vessel wall an intersection point $IP_L$ is defined, as a point located at the minimum distance from the centroid $C_w$ of the guidewire area along the same radial line, to obtain a plurality of intersection points and the method proceeds with the steps from 66 to 68, to close the lumen and define the area and centroid of the lumen.

The image of the step (1) of the lumen segmentation step may be binarized by applying a digital binarization step that uses a multi-level threshold process, in which the light intensity threshold is automatically set by calculating the average light intensity of the OCT image without the guidewire. Thus, a range of intensity values is determined, which may be arranged to match one or more color windows, a color being associated with one light intensity values or a color window being associated with a sub-range of light intensity values.

Preferably, after definition of the perimeter line of the lumen, i.e. at step (3), one or more smoothing algorithms are applied to the image, which compose a contour smoothing filter to be applied to the perimeter line of the lumen as determined in the previous step, e.g. by polygonal approximations or through a low-pass filter, known per se. Alternatively, the smoothing filter is applied after step (1) of the lumen segmentation step and before step (2).

Preferably, after step (2) of the lumen segmentation step and before the step (3) a binary morphological filter is applied using an opening-closing mathematical algorithm to remove the smallest objects (i.e. spurious pixels) and to fill any holes internal to the arterial wall region.

Figure 5:
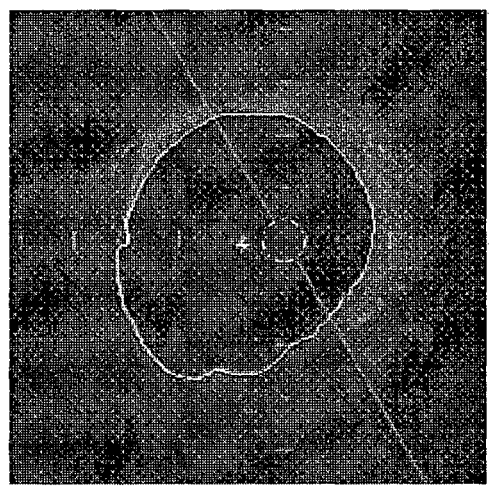
FIG. 5 shows an image obtained by a lumen segmentation step.

FIG. 5 shows an image resulting from lumen segmentation (step 32), in the case of a closed lumen. The solid white line is the result of automatic lumen segmentation on the primary cross-sectional OCT image in which the guidewire has been dimmed, i.e. the definition of the perimeter line of the lumen. The position of the guidewire is indicated in the image with the circle delimited by a dashed line. Through a calibration based on the size of the guidewire, which has a known diameter of 0.48 mm, the lumen area in the image of FIG. 5 was determined to be 6.2 mm².

If the vessel lumen is determined to be open, i.e. if the determination step 31 has a negative result, i.e. at least one discontinuity is visualized in the lumen-delimiting edge, then the method of FIG. 3 initiates a lumen closing procedure, which precedes a lumen segmentation step (which is generally referenced as step 33 in FIG. 3).

Figure 6:
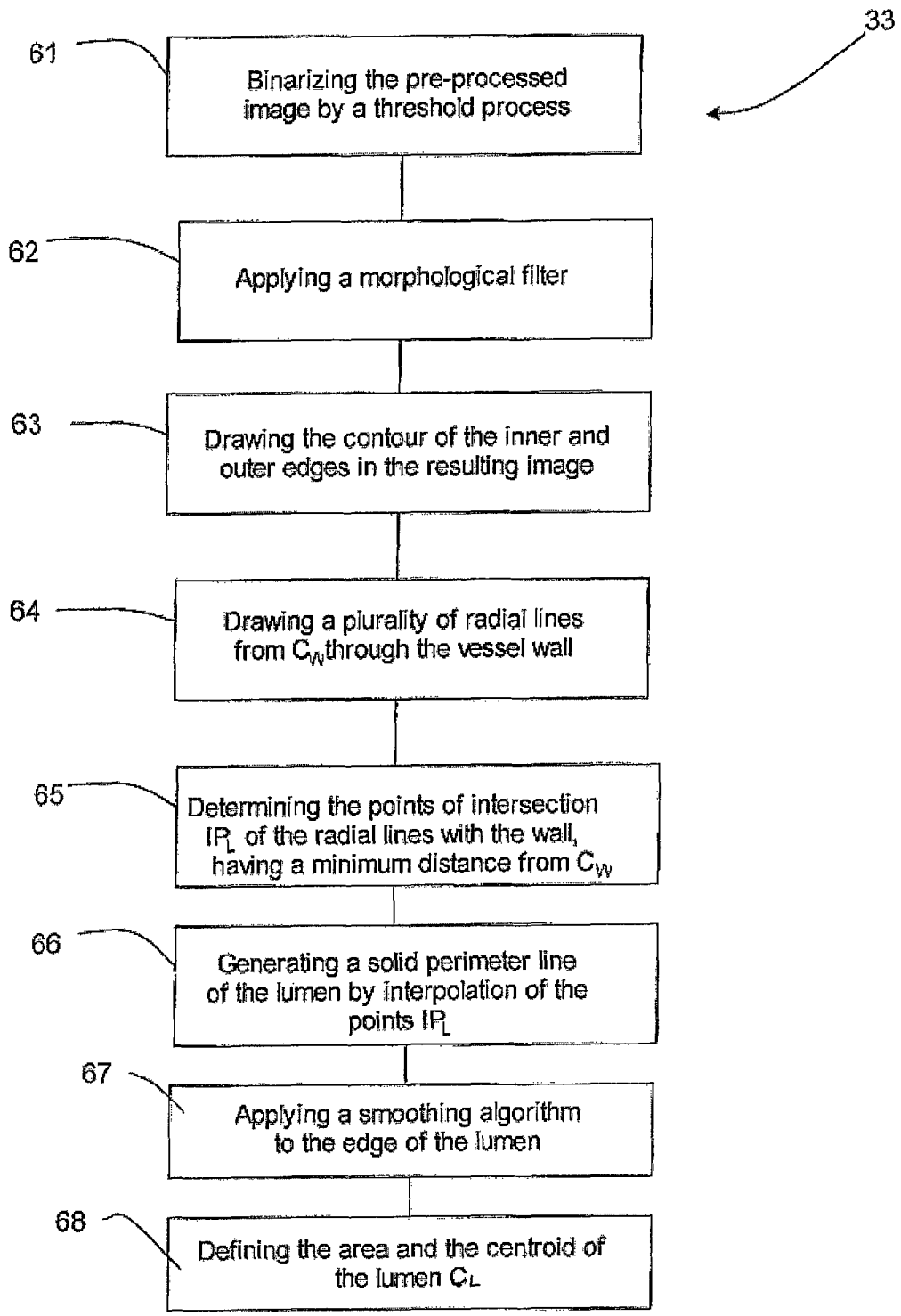
FIG. 6 is a flow diagram of an automatic lumen closing and lumen segmentation procedure according to an embodiment of the invention.

FIG. 6 is a flow diagram of an lumen closing and lumen segmentation procedure 33 according to an embodiment of the invention. The lumen closing procedure comprises converting the image resulting from pre-processing into a binary image, by means of a threshold process (step 61).

In a preferred embodiment, the digital filter using the threshold process of step 61 apply the Otsu method, known per se and described in Otsu, N., "A Threshold Selection Method from Gray-Level Histograms," IEEE Transactions on Systems, Man, and Cybernetics, Vol. 9, No. 1, 1979, pages 62-66, in which an optimal threshold value, is determined by calculating the weighted sum of the variance of pixels attributed to the background and the variance of pixels attributed to objects.

The binary image comprises a region associated to the vessel wall that is highlighted against a background.

Preferably, after the step of binarization of the pre-processed image 61, the lumen closing and segmentation steps involve the application of a mathematical morphological filter using opening-closing mathematical algorithms, known per se, which are based on basic erosion and dilation morphological operations (step 62). The morphological filter introduces a systematic alteration of the geometric content of the image, while maintaining the stability of the important geometric features.

Generally, in the opening-closing algorithm, the opening operation removes small isolated objects (i.e. spurious pixels) and false connections between foreign pixels and is obtained by sequential erosion and dilation operations. The closing operation is obtained by sequential dilation and erosion operations, which enable filling of small dispersed holes and small false discontinuities within objects.

In case of a morphological dilation operator and according to one embodiment, a structuring element S is defined which, when applied to the image I, makes the result of dilation of I with S to be the set of all the translations such that the reflection of S (Ŝ) and I overlap at least at one element.

Formally, the dilation of I with S (structuring element) is given by:

$$I \oplus S = \{z | (\hat{S})_z \cap I \neq 0\}. \quad (2)$$

The dilation I(x,y) by the structuring element S(x, y) provides an output ONE value if, by translation of S(-x,-y) on I(x, y) at least one ONE value is present in the neighborhood of the pixel of interest. For clarity, I(x,y) designates the individual value of the pixel in the binary image in the position (x,y).

The morphological erosion operator, in one embodiment, provides a ZERO value if there is at least one ZERO in the neighborhood and its effect is to remove irrelevant details from an image.

Morphological operators other than those described above may be used.

After application of the morphological filter (step 62), if any, or if no morphological filter is provided, after conversion into a binary image by a threshold process (step 61), a contour of the inner and outer edges of the wall is drawn on the resulting binary image (step 63). Then, the filter is removed by the threshold process, to restore the image resulting from the pre-processing step, on which the previously determined contour of the wall edges is drawn or simply stored if it is not visible. If the step 62 is provided, the pre-processed image contains the transformation created by the morphological filter.

Then, the lumen closing and segmentation procedure comprises the steps of drawing a plurality N of radial lines that pass through the centroid $C_w$ of the guide wire or originate therefrom, and extend through the vessel wall (step 64) and determining a point of intersection of each radial line with the wall as a point having a minimum distance from $C_w$ along the same radial line (step 65).

The process of intersection with a segment of the region that defines the wall and is delimited by the contour of the edges as previously determined in step 63 may result in a plurality of points of intersection with the image region corresponding to the vessel wall for each radial line that has been drawn. The lumen intersection point $IP_L$ is determined as the point of the plurality of intersection points that represents the minimum distance from the centroid $C_w$, along the corresponding radial line. The intersection point may be mathematically represented by the following relation:

$$IP_L = \min(\sqrt{(C_{w_x} - IP_{ix})^2 + (C_{w_y} - IP_{iy})^2}) \quad (3)$$

where i is the number of the intersection points IP; having coordinates $IP_{ix}$ and $IP_{iy}$ for each radial lines and $C_{wx}$ and $C_{wy}$ are the coordinates of the centroid of the guidewire. Preferably, the N radial lines are drawn at a constant angular distance from one another.

Preferably, the plurality of radial lines radially extends over an entire circumference (360° angular distribution). Since the wall area has an open-ring shape, one or more radial lines of the plurality do not intercept the wall region.

The next step is mathematical interpolation of the intersection points $IP_L$ or a sub-set of the points $IP_L$ with a solid contour line, to generate a closed perimeter line of the lumen, by connecting the points $IP_L$ of the open ends of the wall (step 66).

As used herein, the plurality of radial lines are intended to be drawn, like in the other steps of the lumen closing and segmentation procedures, by an automatic procedure, i.e. using a computer.

Preferably, once the perimeter line of the lumen has been generated, one or more smoothing filters are applied to the image, for smoothing the contour of the lumen edge as determined in the previous step, e.g. by a polygonal approximation algorithm or through a low-pass filter, as is known per se (step 67).

Figure 7A:
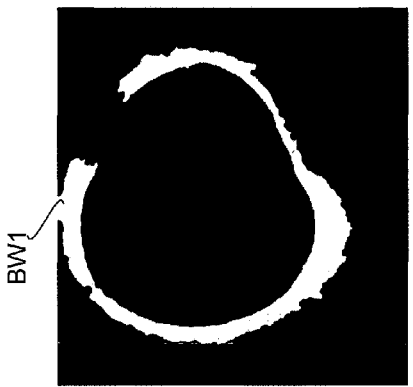
FIGS. 7a-7f shows the images resulting from the main steps of the lumen closing and lumen segmentation procedure in an embodiment of the invention.

FIGS. 7a-7f shows the images resulting from the main steps of the lumen closing and lumen segmentation procedure in an embodiment of the invention. FIG. 7a is the pre-processed primary image in which the centroid $C_w$ of the guide wire has been determined and the guidewire has been dimmed. The arterial wall exhibits a discontinuity caused by a poorly visible wall portion, referenced OP in the figure, in which the inner edge (and possibly the outer edge) is not well defined or is missing. The presence of such discontinuity in an OCT image may be caused by various factors, such as blood corpuscularity in that section of the vessel or the shadow cone of the guidewire.

Figure 7B:
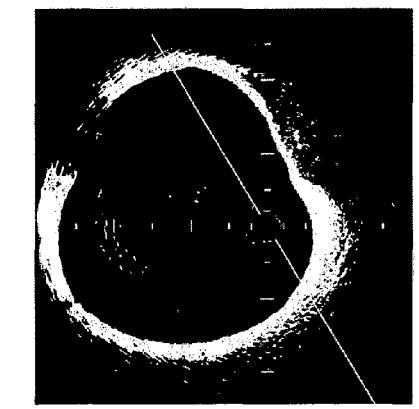
Figure 7C:
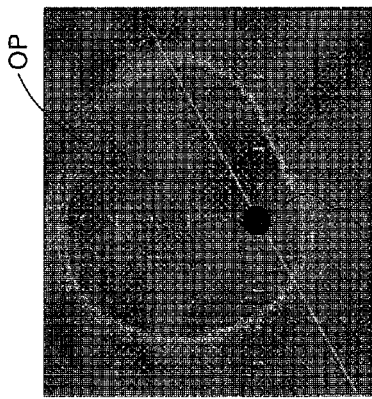
Figure 7D:
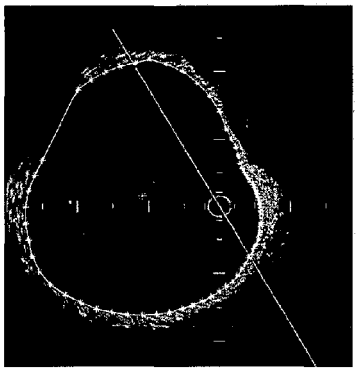
Figure 7E:
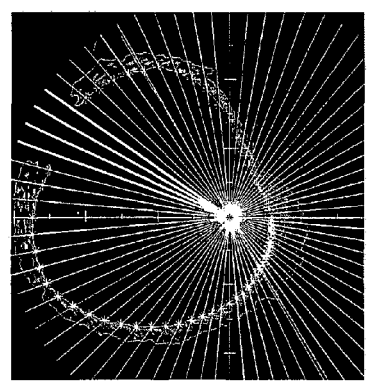
Figure 7F:
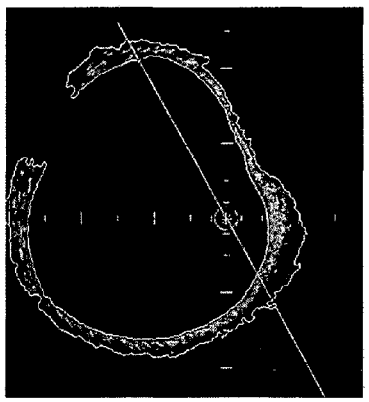

The image of FIG. 7a is the primary image in which the circular mask has been used for guidewire dimming. FIG. 7b is FIG. 7a that has been binarized with the Otsu's method, resulting in a black-and-white image with a single highlighted area, i.e. white over black or black over white. FIG. 7c shows the binarized image of FIG. 7b, with an opening-closing morphological filter, resulting in a black-and-white image with a single area BW1 approximately having an open-ring shape and a white color over a black background. In FIG. 7d binary conversion has been carried out, which restores the light intensity shades of FIG. 7a and the contour of the wall region, determined as a contour of the region BW1 (note that the morphological has not been removed). FIG. 7e is the image of FIG. 7d, upon which a plurality of radial lines have been drawn, originating from the centroid of the guidewire $C_w$ and extending through the wall region. The angular distance between two proximal radial lines is 5°. In FIG. 7e, the thicker white radial lines show the angular sector along which the lumen is open. FIG. 7f shows the line of the lumen perimeter obtained by interpolation and smoothing by applying the Savitzky-Golay filter, as described in Anal. Chem. 36, 1627-1639 (1964), as a fourth grade polynomial model.

Once the perimeter line of the lumen has been determined, in both closed lumen and open lumen cases, the area of the lumen may be automatically determined, and the centroid of the lumen, $C_L$, defined as the center of mass of the lumen area may be derived therefrom.

When the perimeter line of the lumen and the centroid of the lumen resulting from the lumen segmentation process, i.e. obtained from a first lumen segmentation procedure if the lumen is closed or a second lumen segmentation procedure following a lumen closing procedure if the lumen is open, the method comprises a step of automatically finding (or segmenting) an outer edge of the vessel wall. Referring back to FIG. 3, the outer edge segmentation step is referenced 34.

The segmentation of the outer edge of the vessel accounts for the typical depth that is reached by the OCT signal in the tissues, i.e. 1.0-1.3 mm, as reported, for instance, in the above mentioned review by Prati et al.

The outer edge segmentation step comprises:
selecting a preset vessel wall thickness value;
after selecting a preset wall thickness value, drawing a plurality of radial lines originating from the centroid of the lumen, $C_L$, and extending through the vessel wall;
determining the point of intersection of each radial line with the perimeter line of the lumen;
determining an external point $IP_E$ by adding the preset thickness value from the intersection point between such radial line and the perimeter line of the lumen, and
defining an outer perimeter line of the vessel wall by joining the points $IP_E$ identified for each radial line.

The radial distribution of radial lines is circumferential, such that the entire contour of the outer edge may be defined.

The wall thickness imposed in the outer edge segmentation step is selected considering the typical thicknesses of "normal" vessels affected by anomalies, such as atherosclerotic plaques, to cover an area that has a very high probability of comprising all the possible wall tissues that compose the cross section of the vessel, as visualized in the analyzed OCT image. For example, the wall thickness is selected to be equal to 1 mm. The preset thickness value in physical units of measurement is converted into pixel coordinates by calibration, referenced 43 in FIG. 3.

Preferably, following generation of the outer perimeter line, one or more smoothing filters are applied to the image, for smoothing the contour of the lumen edge as determined in the previous step, e.g. by a polygonal approximation algorithm or through a low-pass filter, known per se. In this case, the outer perimeter line of the vessel is given by the function resulting from the smoothing algorithm/s.

The area between the two inner and outer perimeter lines defines a first region of interest, $ROI_1$, enclosing the tissues of the vessel wall, which will be processed in the later segmentation steps.

Figure 8B:
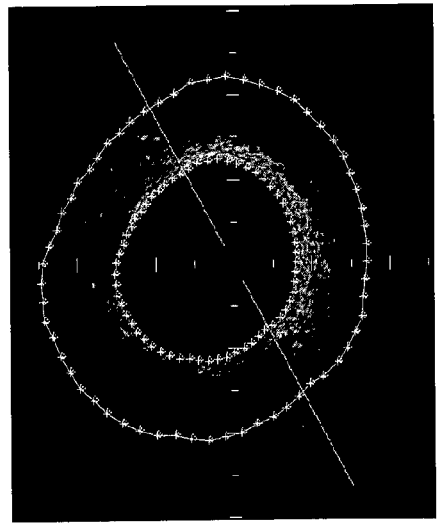
FIG. 8b shows the result of the outer edge segmentation applied to the image of FIG. 8a, with the perimeter line of the lumen, or inner edge of the vessel wall, and the perimeter line of the outer edge being visible therein.
Figure 8C:
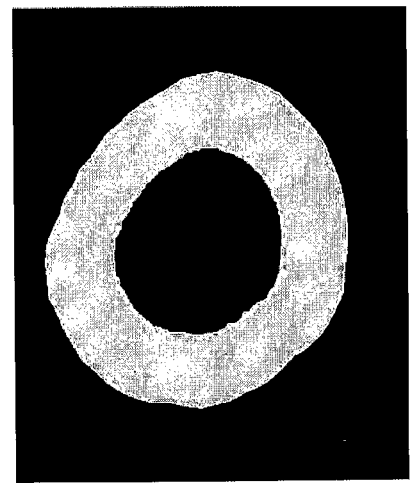
FIG. 8c shows the thickness of the first region of interest, delimited by the perimeter line of the lumen and the outer edge as shown in FIG. 8b.
Figure 8A:
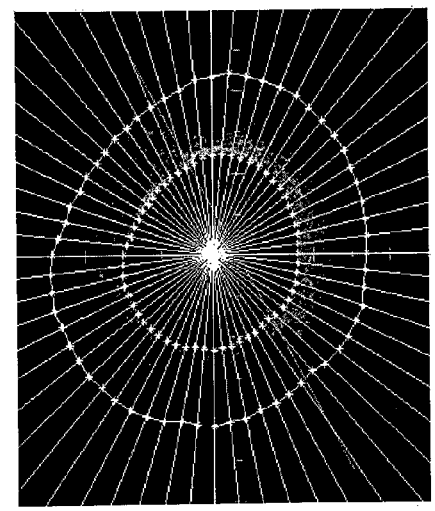
FIG. 8a is an image of a vessel section after the lumen segmentation step, upon which a plurality of (white) radial lines have been drawn, originating from the centroid of the lumen, to determine an outer edge of the vessel wall.

FIG. 8a is a cross-sectional OCT image of a vessel section after the lumen segmentation step, upon which a plurality of (white) radial lines have been drawn, originating from the centroid of the lumen. Each radial line intercepts one point of the perimeter line of the lumen, as determined in the previous lumen segmentation step (the points of the perimeter line of the lumen are designated in FIG. 8a by squares). The angular distance between radial lines is 6°. For each point of the perimeter line intercepted by a radial line, the preset thickness value is added, i.e. 1 mm in this example, along such radial line, which will provide an outer edge point $IP_E$ (the outer edge points are also designated in the image by squares). The connection of outer edge points define the perimeter line of the outer edge of the vessel, as shown in the figure by the solid lines that join the points $IP_E$ together.

FIG. 8b shows the result of the outer edge segmentation, with the perimeter line of the lumen, or inner edge of the vessel wall, and the perimeter line of the outer edge being visible therein. The $ROI_1$ has an approximately annular shape and is defined as the area between the perimeter line of the lumen and of the outer edge (FIG. 8c). Particularly, in FIG. 8c, the $ROI_1$ is visualized as a single grey area, against a black background. The $ROI_1$ may be conveniently visualized as a binary image to assess its shape, as well as any anomaly caused, for instance by the presence of artifacts that were not visible in the previous steps.

Referring now to FIG. 3, after the outer edge segmentation step, the processing method comprises a fibrous plaque segmentation step (step 35). The fibrous plaque is found in the first region of interest $ROI_1$ as a homogeneous high-reflectivity region.

The fibrous plaque segmentation step comprises:
applying a digital decorrelation stretching filter to increase contrast of neighboring elements in the $ROI_1$ and highlight homogeneous light intensity regions;
automatically selecting at least one homogeneous image region having an intensity that exceeds a preset value, using a binarization filter;
applying an opening-closing morphological filter to the homogeneous region;
creating a contour for the homogeneous region, e.g. by automatically drawing a solid line that delimits the region highlighted by the binarization filter and the morphological filter, and identifying the resulting homogeneous region as a second area of interest $ROI_2$.

In FIG. 3, Identification of the second area of interest occurs in step 38.

Examples of decorrelation stretching filters are described in N. Cambell, "*The decorrelation stretch transformation*" Int. J. Remote Sensing, vol. 17, pp. 1939-1949, 1996 and in Dasu et al, "*An Application of Decorrelation and Linear Contrast Stretching Methods on Satellite Images*", VSRD-IJEECE, Vol. 1 (7), 2011, 402-410.

In the image resulting from the fibrous plaque segmentation step, a homogeneous high-light intensity region is determined and contoured, i.e. a second area of interest $ROI_2$.

It shall be noted that the step 35 in the processing method is indicated as a fibrous plaque segmentation step, as the mainly fibrous tissue plaque generally represents a very bright region proximate to the lumen. Nevertheless, the method shall not be intended to the limited to the high-reflectivity nature of the tissue contained in the region segmented in step 35.

After fibrous plaque segmentation, in the preferred embodiments, the method proceeds with a step of quantification of the extent of the fibrous plaque region, referenced 39 in FIG. 3. Since the fibrous tissue is generally distributed in a region that surrounds a radial lumen portion, the angular extent of the fibrous plaque region is advantageously calculated. The quantification of the angular extent of the fibrous plaque region comprises:

drawing a plurality of radial lines originating from the centroid $C_L$ of the lumen and extending along the vessel wall (e.g. through the previously defined $ROI_1$) the plurality of radial lines having an angular distribution with an angular pitch defined between two proximal radial lines;

determining, for each radial line of the plurality, whether such radial line intercepts one point of the fibrous plaque region, selecting a sub-plurality of radial lines, which intercept a point of the fibrous plaque region, and;

determining the angular extent of fibrous plaque region according to the number of the sub-plurality of radial lines and the angular pitch between two proximal radial lines of the sub-plurality.

The radial lines originating from or passing through the centroid of the lumen preferably have a constant angular pitch.

Assuming that $n_0$ is the number of the plurality of radial lines drawn on the image in the fibrous plaque quantification step and $n_f$ is the number of the sub-plurality of radial lines that intercept at least one point of the fibrous plaque region, the angular extent, $\theta_f$, of the fibrous plaque region falls within the range of values given by the following relation:

$$(n_0 - 1)\frac{360°}{n_f} \leq \vartheta_f < (n_0 + 1)\frac{360°}{n_f}. \qquad (4)$$

The resolution of measurement depends on the angular pitch that has been used in the procedure.

If the radial extent of the fibrous plaque region and/or the thickness of such region has to be determined in linear units of measurement (e.g. mm), the coordinates of one pixel must be converted into a physical measurement unit through a calibration step. In one embodiment, the calibration of each OCT image, that allows conversion of the coordinates of one pixel into a physical unit of measurement is based on the knowledge of the physical size of the guidewire, as determined in step 43 of FIG. 3. Alternatively, a calibration segment having a known physical dimension may be used for OCT image calibration.

Figure 9A:
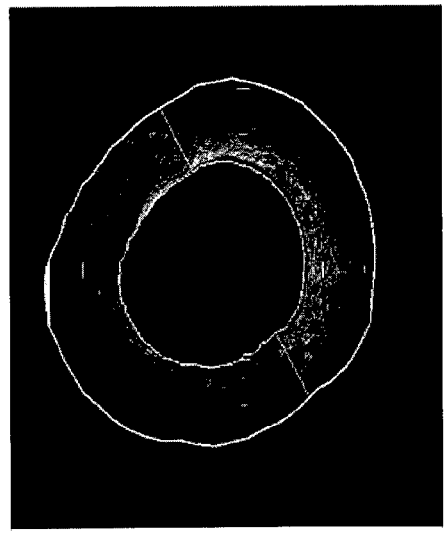
FIGS. 9a-9d show the images resulting from the main steps of the fibrous plaque segmentation step.

FIGS. 9a-9d show the cross-sectional OCT images resulting from the main steps of the fibrous plaque segmentation step. FIGS. 9a-9d derive from the same primary image as that of FIGS. 8a and 8b. Particularly, FIG. 9a shows by way of example the image of FIG. 8b, overlapped by the $ROI_1$.

Figure 9B:
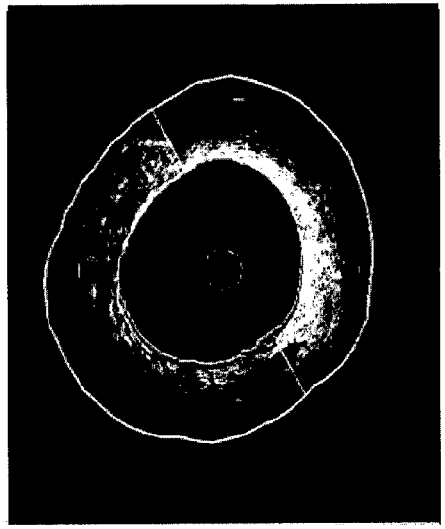

In FIG. 9b, once the image of FIG. 8b has been restored, a decorrelation stretching filter has been applied to the $ROI_1$. In the image resulting from FIG. 9b, the filter has highlighted a region, having a bright color in the image, which extends into a region surrounding a lower and lateral lumen portion. This brighter region is generally associated with a mainly fibrous tissue. An approximately circular dark gray region in the lumen overlaps the image and indicates the position of the guidewire, that is dimmed in the image.

Figure 9C:
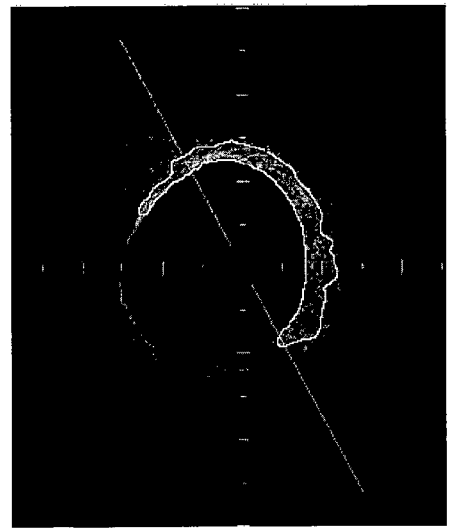

FIG. 9c shows the result of fibrous plaque segmentation (i.e. the definition of $ROI_2$) after application of morphological operators for erosion of spurious pixels to the image of FIG. 9b (the characteristics of the vessel wall not included in the high intensity region have been moved to the background) and the contour detection for such region.

Figure 9D:
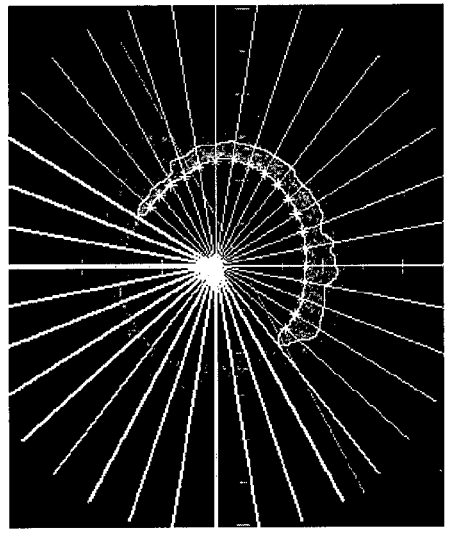

FIG. 9d shows the image of FIG. 9c, upon which a plurality of radial lines have been drawn, originating from the center of the lumen and extending radially outwards. The white radial lines represent the lines that do not intercept the fibrous plaque region, whereas the bright gray radial lines represent the sub-plurality of lines that intercept such region. The angular pitch between the lines is 10°. The angular extent of the fibrous plaque region is $\theta_f \geq 180°$. Through a calibration based on the size of the guidewire, which has a known diameter of 0.48 mm, the area of the fibrotic plaque region is 3.2 mm².

After the fibrous plaque segmentation step, the method comprises a step for segmenting the calcific or lipid plaque, that contains mainly calcific or lipid tissues or the fibrocalcific plaque, that contains both fibrous and calcific tissue. This step is referred to in this disclosure and the claims as a hyporeflective plaque segmentation step, and is referenced 37 in FIG. 3. In a cross-sectional OCT image, a lesion or anomaly of a mainly calcific and/or lipid tissue is often difficult to visualize or highlight, as such tissues are hyporeflective in an OCT image.

Considering the difficulty of automatically and accurately isolating a hyporeflective region of the vessel wall, the hyporeflective plaque segmentation steps carries out a semi-automatic process in which, after fibrous plaque segmentation, a first detection of the image region containing the calcific plaque is manually carried out by an operator. The hyporeflective plaque segmentation step comprises:

preferably applying a color filter or a threshold process filter to the image resulting from the fibrous plaque segmentation step, to partially dim the previously segmented fibrous plaque region (i.e. $ROI_2$);

manually defining by a user a preliminary hyporeflective region, $\Omega_0$, which contains vessel wall tissues and is external to the fibrous plaque, such preliminary region having a contour;

automatically checking whether the preliminary region $\Omega_0$ falls within the first region of interest $ROI_1$;

in the negative, repeating the step of manually defining a preliminary region;

in the positive, automatically carrying out the following steps (using a computer):

storing the contour of the preliminary hyporeflective region;

calculating a maximum light intensity value, a minimum light intensity value and a mean intensity value between the maximum value and the minimum value, within the preliminary region;

converting the image into a binary image by means of a band-pass threshold filter that selects the intensity values ranging between the maximum intensity value and the mean intensity value to identify image portions having a prevailing fibrous component within the preliminary region;

applying a closing morphological filter, for filling the holes in image portions having a fibrous component, and applying a convex hull morphological filter, to define a homogeneous region having a continuous contour.

Preferably, the contour of the preliminary region is a closed contour, e.g. defining a polygon.

The preliminary hyporeflective region may be manually defined by drawing a plurality of segments that form a closed polygon. In this case, the computer receives from an operator geometric data concerning the plurality of successive segments that define a closed polygon, i.e. the preliminary hyporeflective region $\Omega_0$. This region may be considered as an "initial guess" of the region that contains the fibrocalcific plaque, i.e. the hyporeflective plaque. In good approximation, since the tissues having a calcific component usually have well defined contours, the regions having a mainly calcific component may be deemed to be the filling and closing areas resulting from application of the morphological filter.

In one embodiment, the regions having a mainly calcific (or lipid) component are defined assuming the penetration capacity of the OCT system that has generated the image (e.g. 1 mm).

With $FC_f$ being the area of the fibrous tissue defined by the above described threshold process, L being the area of the lumen and $F_t$ being the area of the fibrous plaque (i.e. $ROI_2$) as previously determined, the area of the calcific tissue $FC_c$ is given by the convex hull (convex hull), H, of the area $FC_f$ less the areas L and $F_t$, i.e.:

$$FC_c = H(FC_f) - (L \cup F_t). \quad (5)$$

The relation (5) is also true for a region having a mainly lipid or a mainly calcific component.

Figure 10A:
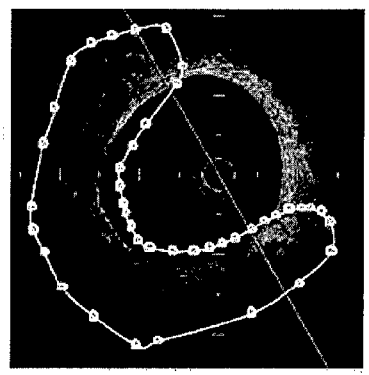
FIGS. 10a-10d show the images resulting from the main steps of the fibrocalcific plaque segmentation step.

FIGS. 10a-10d show the cross-sectional OCT images resulting from the main steps of the fibrocalcific plaque segmentation step. FIGS. 10a-10d derive from the same primary image as that of FIGS. 8a and 8b and 9a-9d. Particularly, FIG. 10a shows by way of example the image of FIG. 9c, in which the $ROI_1$ and the $ROI_2$ overlap, and in which the fibrous plaque ($ROI_2$) has been dimmed.

Figure 10B:
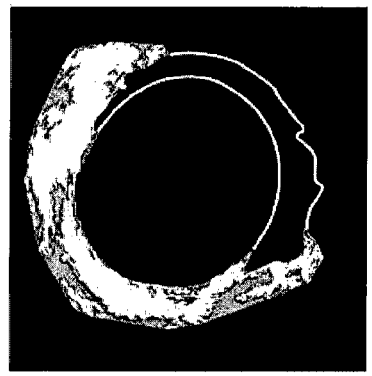

FIG. 10b shows the image of FIG. 10a less the $ROI_1$ and the $ROI_2$, with a preliminary hyporeflective region containing fibrocalcific tissues having been manually defined thereon, by drawing a succession of segments that form a polygon. Small circles define the ends of the segments.

For example, the segments may be selected using a mouse connected to the computer or on the screen that displays the image, if the screen is a touch-screen. The successive segments form a closed traverse, as shown by way of example in FIG. 10b, which defines the preliminary region, or "initial guess", $\Omega_0$. As noted in the example of FIG. 10b, the preliminary region also includes part of the area of the lumen L and part of the area of the fibrous plaque $F_t$. Then, the areas L and are removed with the subtraction operation of Eq. (5).

Figure 10C:
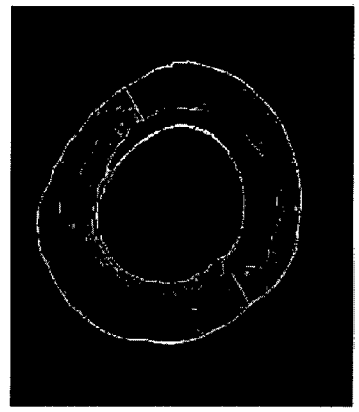

FIG. 10c shows a binary image resulting from the application of the threshold process filter to the preliminary region. The area having light intensity values ranging from the maximum intensity value to a mean value, as automatically determined by the digital filter, is shown in white color. The white area may be associated with the fibrous component of the hyporeflective region.

Figure 10D:
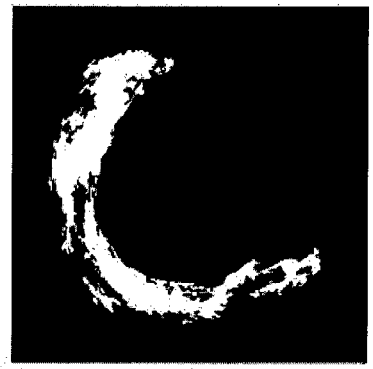

FIG. 10d shows the image resulting from the application of closing morphological filters and of complex hull morphological filters to the image of FIG. 10c. The completion area resulting from the application of the morphological filters is shown in grey. The contour of the fibrous plaque as previously determined overlaps the image of FIG. 10d.

Full segmentation from a primary image to the result of FIG. 10d for a single cross-sectional image was carried out in a computational time of about 15 s using a workstation with an Intel Core 2 Quad processor. Conversely, it shall be noted that an entirely manual segmentation by a skilled operator may require several minutes.

It should be understood that, while the example of FIGS. 9a-9f relates to an OCT image of a vessel section in which the fibrous component extends to a radial external portion of the lumen, the present method allows segmentation of fibrous and hyporeflective plaques even with a different distribution of microstructures in a vessel section. For instance, the method may be implemented on an OCT image in which the fibrous plaque extends along the entire circumference of the intima, with one or more lipid or calcific (hyporeflective) plaques surrounding the fibrous plaque.

After hyporeflective plaque segmentation, the method preferably proceeds to a step of quantification of the extent of the hyporeflective plaque (referenced 41 in FIG. 3).

The hyporeflective plaque quantification step comprises:
  drawing a plurality of radial lines that pass through the centroid $C_L$ of the lumen and extending along the vessel wall, the plurality of radial lines having an angular distribution with an angular pitch defined between two proximal radial lines;
  determining, for each radial line of the plurality, whether such line intercepts one point of the hyporeflective plaque region;
  selecting a sub-plurality of radial lines, which intercept a point of the hyporeflective plaque region, and
  determining the angular extent of hyporeflective plaque region based on the number of the sub-plurality of radial lines and of the angular pitch between two proximal radial lines of the sub-plurality.

The radial lines originating from or passing through the centroid of the lumen preferably have a constant angular pitch.

Assuming that $n_0$ is the number of the plurality of radial lines drawn on the image in the step of quantification of the extent of the fibrocalcific plaque and $n_f$ is the number of the sub-plurality of radial lines that intercept one point of the fibrocalcific plaque region, the angular extent, $\theta_{fc}$, of the fibrocalcific plaque region falls within the range of values given by the following relation:

$$(n_0 - 1)\frac{360°}{n_{fc}} \leq \theta_{fc} < (n_0 + 1)\frac{360°}{n_{fc}}. \quad (6)$$

The extent of the hyporeflective plaque, e.g. its thickness, is quantified in metric units of measurement by a calibration step, referenced 43 in FIG. 3, which converts the pixel coordinates into linear units of measurement.

Figure 11C:
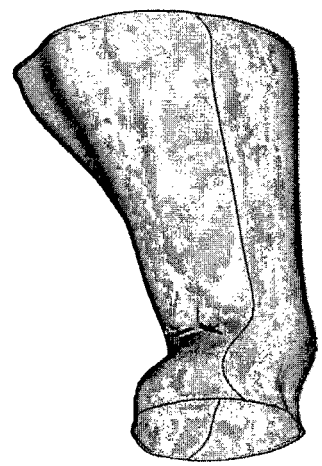
FIGS. 11a-11c show the result of lumen segmentation in 10 cross sections of the same vessel (FIG. 11a), the result of NURBS creation on the segmentation of FIG. 11a (FIG. 11b) and the result of the surface in IGES format (FIG. 11c) for possible exportation of the lumen into numerical simulation codes.
Figure 11B:
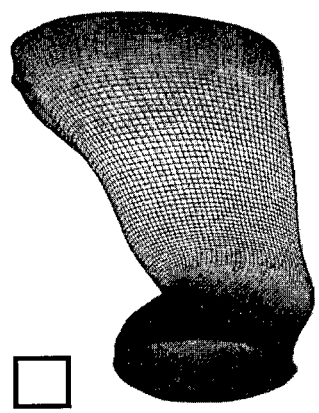
Figure 11A:
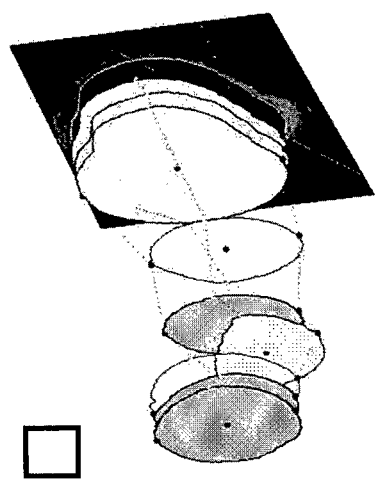

The cross-sectional OCT images are two-dimensional images of a section of a blood vessel, e.g. a coronary artery. From a number of cross-sectional images acquired in various longitudinal positions of the blood vessels, a 3D image of the blood vessel and its anomalies may be reconstructed. For example, FIGS. 11a-11b show graphical reconstructions obtained by structural finite-element modeling. Namely, in FIG. 11a a plurality of cross-sectional OCT images processed by the method of the present invention have been graphically reconstructed and introduced as an input into a commercial structural finite-element modeling software system. FIG. 11b shows the graphical reconstruction of a 3D NURBS surface geometric modeling of the cross-sectional images of FIG. 10a. FIG. 11c shows the graphical reconstruction of a 3D NURBS surface geometric modeling in which data has been imported in IGES format. The method of the preferred embodiments of the present invention allows processing of cross-sectional OCT images having common artifacts, such as blood residues in a vessel, guidewire-lumen contact, irregular edges and open lumen.

Also, it is possible to obtain a high-quality segmentation of the main microstructures of a coronary vessel in a relatively short time, e.g. from 10 to 20 seconds.

The invention claimed is:

1. A semiautomatic method of processing intravascular Optical Coherence Tomography (OCT) images, comprising:
   receiving in a computer a primary cross-sectional OCT image visualising a section of a blood vessel having a lumen and a vessel wall;
   pre-processing the primary image by the computer, wherein the pre-processing step comprises segmenting a guide wire in the lumen and excluding the guide wire from the primary image to obtain a pre-processed image;
   determining whether the lumen is closed;
   if the lumen is determined to be closed, performing a first automatic lumen segmentation procedure on the pre-processed image to define a perimeter line of the lumen, corresponding to the inner edge of the vessel wall, and determine a centroid $C_L$ of the lumen area;
   if the lumen is determined not to be closed, sequentially performing an automatic lumen closing procedure on the pre-processed image, and a second automatic lumen segmentation procedure, to define a perimeter line of the lumen, corresponding to the inner edge of the vessel wall, and determine a centroid $C_L$ of the lumen area;
   automatically finding an outer edge of the vessel wall and defining a first region of interest $ROI_1$ between the inner edge and the outer edge of the lumen;
   automatically segmenting a fibrous plaque in the first region of interest $ROI_1$, thereby defining a second region of interest $ROI_2$ that contains the fibrous plaque, and segmenting a hyporeflective plaque, contained in a radial region that falls within $ROI_1$ and is external to $ROI_2$.

2. The method of claim 1, wherein determining if the lumen is closed is carried out by an automatic process.

3. The method according to claim 1, wherein segmenting a hyporeflective plaque is carried out by a semi-automatic process in which a first detection of the image region containing the hyporeflective plaque is manually carried out by an operator.

4. The method according to claim 1 wherein, in the step of pre-processing the primary image, the step of segmenting the guide wire comprises:
   creating a sub-image in a central portion of the primary image;
   transforming said sub-image into a binary image using a digital binarization filter that defines a light intensity threshold value or a range of light intensity threshold values to generate a sample image highlighting one or more regions having a high light intensity relative to a background;
   applying a morphological filter to the sample image, which filter sequentially uses a morphological operator of recognition and extraction of objects having a round shape and a morphological erosion operator to eliminate small non-round objects so as to identify a round object associated with the guide wire; and
   calculating the area of the round object so identified and calculating a local centroid $C_W$ of said area.

5. The method as claimed in claim 4 wherein, in the step of pre-processing the primary image, the step of excluding the guide wire from the primary image comprises:
   restoring the primary image, and
   subtracting the round object associated with the previously segmented guide wire from the primary image to generate a subtraction image corresponding to the pre-processed image.

6. The method as claimed in claim 4, wherein the step of creating a sub-image in a central portion of the primary image is carried out in accordance with one of the following steps:
   applying a digital crop filter by a process of selection and extraction of a central primary image portion from the primary image, and
   selecting by an operator an image portion in the lumen.

7. The method as claimed in claim 1, wherein the first automatic lumen segmentation procedure comprises:
   transforming the pre-processed image into a binary image using a digital binarization filter, to define an annular vessel wall region relative to a background,
   defining a lumen area as an area of an image portion enclosed and delimited by the annular vessel wall region;
   defining a perimeter line of the lumen, which corresponds to the contour of the lumen area, and
   determining a centroid $C_L$ of the lumen area.

8. The method as claimed in claim 1, wherein the step of segmenting the guide wire comprises defining a centroid $C_W$ of the guide wire area, and wherein the automatic lumen closing procedure and the second automatic lumen segmentation procedure comprise:
   transforming the image resulting from the pre-processing step into a binary image, by applying a digital binarization filter that generates a region BW1 associated with the vessel wall highlighted against a background, the region BW1 exhibiting a radial discontinuity in light intensity, in at least one radial portion of the lumen;
   contouring the BW1 region on the binary image;
   drawing a plurality of radial lines originating from the centroid $C_W$ of the guide wire and radially extending through the region BW1;
   determining an intersection point $IP_L$ between each radial line and the wall as a point having the minimum distance from the centroid $C_W$ of the guide wire area along the same radial line to obtain a plurality of intersection points $IP_L$;
   generating a perimeter line for closing the lumen by interpolation of the intersection points $IP_L$, and
   calculating the lumen area as an area enclosed and delimited by the perimeter closing line and determining a centroid $C_L$ of the lumen area.

9. The method as claimed in claim 8, which further comprises, after converting the pre-processed image into a binary image and before contouring the region BW1, applying an opening-closing morphological filter to the region BW1.

10. The method as claimed in claim 1, wherein automatically finding an outer edge of the vessel wall and defining a first region of interest $ROI_1$ comprises:
    selecting a preset wall thickness value;
    drawing a plurality of radial lines originating from the centroid $C_L$ of the lumen area and extending through the vessel wall, the plurality of radial lines having a radial distribution extending along a circumference;
    determining the intersection point between each radial line and the perimeter line of the lumen, the perimeter line as determined in the first or in the second automatic segmentation procedure;
    determining an external point $IP_E$ by adding, along each radial line, the preset thickness value from the intersection point between such radial line and the perimeter line of the lumen;
    defining an outer edge as the perimeter line obtained by joining the points $IP_E$ identified for each radial line, and defining a first region of interest $ROI_1$ as an image portion delimited by the perimeter line of the lumen and the outer edge.

11. The method as claimed in claim 1, wherein the step of automatically segmenting the fibrous plaque comprises:
applying a digital decorrelation stretching filter in the first region of interest $ROI_1$;
selecting a homogeneous image region having an intensity higher than a preset threshold value by applying a binarization filter to the image resulting from the application of the digital decorrelation stretching filter;
applying an opening-closing morphological filter to the homogeneous region;
contouring the homogeneous region, and
identifying the resulting homogeneous region as the second region of interest $ROI_2$.

12. The method as claimed in claim 11, which further comprises, after the step of segmenting the fibrous plaque, a step of automatically quantifying the angular extent of the fibrous plaque region comprising:
drawing a plurality of radial lines originating from the centroid $C_L$ of the lumen area and extending through the $ROI_1$, the plurality of radial lines having an angular distribution with an angular pitch defined between two proximal radial lines;
determining, for each radial line of the plurality, whether such radial line intercepts one point of the fibrous plaque region;
selecting a sub-plurality of radial lines, which intercept the second region of interest $ROI_2$ and
determining the angular extent of $ROI_2$ according to the number of the sub-plurality of radial lines and the angular pitch between two proximal radial lines of the sub-plurality.

13. The method as claimed in claim 1, wherein the step of segmenting the hypo-reflective plaque comprises:
receiving, by an operator, geometric data defining a preliminary hyporeflective region that contains vessel wall tissues and is external to the second region of interest $ROI_2$, wherein the preliminary region has a contour;
automatically checking whether the preliminary region falls within the first region of interest $ROI_1$;
in the negative, repeating the step of receiving geometric data;
in the positive, automatically carrying out the steps of:
storing the contour of the preliminary region;
calculating a maximum light intensity value, a minimum light intensity value and a mean intensity value between the maximum and minimum values, within the preliminary region;
transforming the image into a binary image by means of a band-pass threshold filter that selects the intensity values ranging between the maximum intensity value and the mean intensity value to identify image portions having a prevailing fibrous component within the preliminary region, and
applying a convex hull morphological filter to define a hyporeflective plaque region having a continuous contour.

14. The method as claimed in claim 13, wherein the step of segmenting the hyporeflective plaque comprises, before the step of receiving geometric data defining a preliminary hyporeflective region, a step of automatically obscuring at least partially the second region of interest $ROI_2$.

15. The method as claimed in claim 13, which further comprises, after the step of segmenting the hyporeflective plaque, a step of automatically quantifying the hyporeflective plaque, which in turn comprises:
drawing a plurality of radial lines which pass through the centroid $C_L$, of the lumen area and radially extend at least through the hyporeflective plaque region, the plurality of radial lines having an angular distribution with an angular pitch between two proximal radial lines;
determining, for each radial line of the plurality, whether such line intercepts one point of the hyporeflective plaque region;
selecting a sub-plurality of radial lines which intercept the hyporeflective plaque region, and
determining the angular extent of the hyporeflective plaque region according to the number of the sub-plurality of radial lines and the angular pitch between two proximal radial lines of the sub-plurality.

\* \* \* \* \*